United States Patent [19]

Greatbatch

[11] 4,135,519

[45] Jan. 23, 1979

[54] CARDIAC PACER HAVING ALKALI METAL-HALOGEN CELL WITH MIXED HALOGEN CATHODE

[76] Inventor: Wilson Greatbatch, 5220 Donnington Rd., Clarence, N.Y. 14031

[21] Appl. No.: 853,136

[22] Filed: Nov. 21, 1977

[51] Int. Cl.$^2$ .............................................. A61N 1/36
[52] U.S. Cl. ............................. 128/419 PS; 429/193; 429/199
[58] Field of Search ....... 128/419 P, 419 PG, 419 PS; 429/191, 193, 199

[56] References Cited

U.S. PATENT DOCUMENTS

| | | | |
|---|---|---|---|
| 3,757,793 | 9/1973 | Fester et al. .................. | 128/419 PS |
| 3,976,505 | 8/1976 | Farrington et al. ................. | 429/193 |
| 3,981,746 | 9/1976 | Margalit ................ | 429/199 |

OTHER PUBLICATIONS

Greatbatch et al., "IEEE Transactions on Biomedical Engineering", vol. 18, No. 5, Sep. 1971, pp. 317-323.

Primary Examiner—William E. Kamm
Attorney, Agent, or Firm—Christel & Bean

[57] ABSTRACT

A cardiac pacer having an alkali metal-halogen cell comprising an alkali metal anode, preferably lithium, a solid alkali metal-halogen electrolyte and a cathode comprising a mixture of two halogens, for example iodine and bromine, the two halogens providing discharge of the cell at two different levels of cell output voltage. The two halogens are in different proportions by weight of the mixture thereby providing a two step output voltage-time characteristic. The second step or plateau in the output voltage characteristic provides an early warning of pacer battery exhaustion.

6 Claims, 5 Drawing Figures

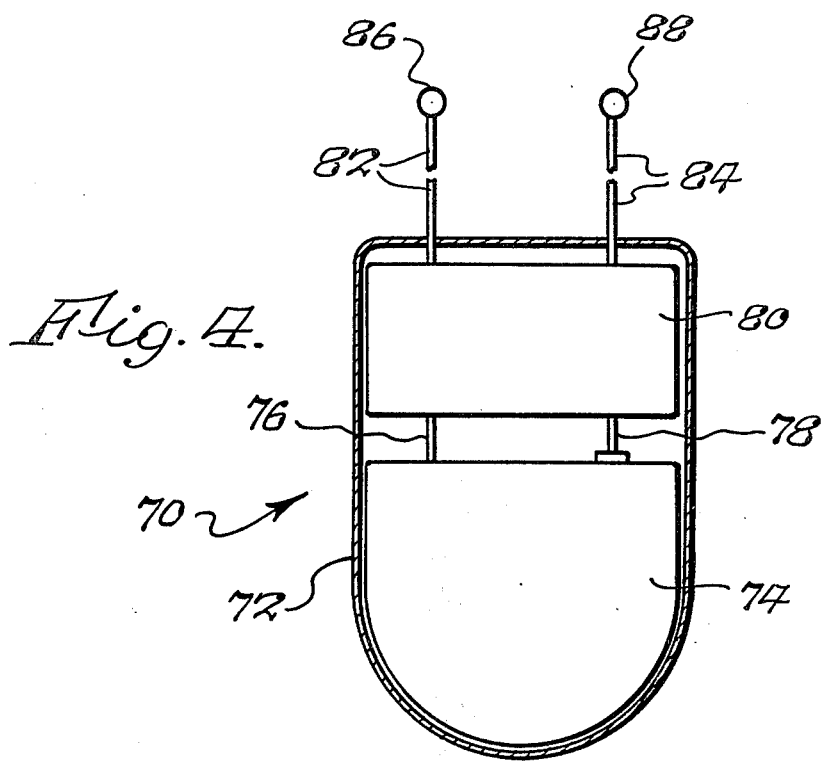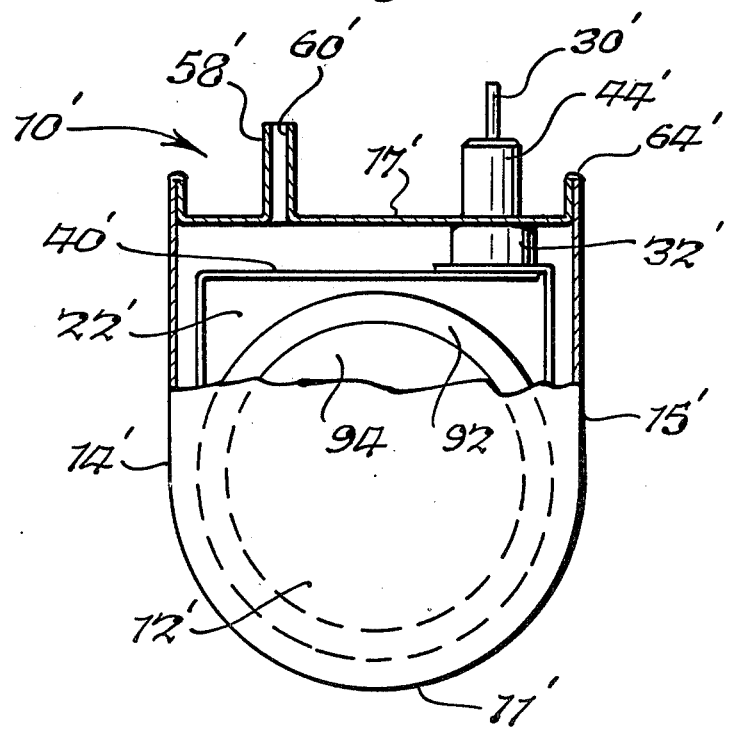

CARDIAC PACER HAVING ALKALI METAL-HALOGEN CELL WITH MIXED HALOGEN CATHODE

BACKGROUND OF THE INVENTION

This invention relates to the conversion of chemical energy to electrical energy, and more particularly to a solid electrolyte primary cell for use in a cardiac pacer and having a lithium anode, a halogen mixture cathode and a lithium halogen electrolyte.

In recent times a solid electrolyte primary battery has been developed to provide relatively high voltage and high energy density in a battery which is especially useful for long life, low current drain applications such as an implanted cardiac pacer. Of the alkali metals, lithium is generally recognized as the most satisfactory material for the negative electrode, i.e. the anode on discharge, in a non-aqueous cell. In selecting material for the positive electrode, i.e. cathode on discharge, it is appropriate to consider, among other factors, relative chemical activity, energy density and discharge characteristic during cell life.

SUMMARY OF THE INVENTION

It is, therefore, an object of this invention to provide a new and improved solid electrolyte cell having relatively high voltage and high energy density, and being especially useful for long life, low current drain applications such as an implanted cardiac pacer.

It is a further object of this invention to provide such a cell which provides an indication or warning when the cell is near end of life.

It is a further object of this invention to provide such a cell having an output voltage characteristic which decreases in a step-wise rather than abrupt manner.

It is further object of this invention to provide such a cell which can be tested for self discharge condition in a non-destructive manner.

It is a further object of this invention to provide a lithium-iodine cell having a cathode including a charge transfer complex of an organic electron donor and iodine wherein the complex is formed in situ.

It is a further object of this invention to provide an improved lithium-halogen cell for use in an artificial cardiac pacer.

The present invention provides a cardiac pacer having an alkali metal-halogen cell comprising an anode of alkali metal, preferably lithium, a solid alkali metal-halogen electrolyte and a cathode comprising a mixture of two halogens, one of the halogens providing discharge of the cell at a first level of cell output voltage and the other of the halogens providing discharge of the cell at a second level of cell output voltage. In one aspect, the halogen which provides cell discharge at the higher level of cell output voltage, i.e. the more active halogen, is in the greater proportion by weight of the mixture. The two step discharge characteristic provides a lower output voltage plateau near the end of cell life which gives an early warning of impending cell exhaustion and softens the impact of exhaustion of the upper level discharge. In another aspect, the halogen which provides cell discharge at the higher output voltage level is in the lesser proportion by weight of the mixture. The relatively higher output voltage plateau of short time duration can be used in non-destructive testing for self-discharge. The cell serves as the pacer voltage source which is connected to the input of a pulse forming means, the output of which is connected to patient electrodes.

The foregoing and additional advantages and characterizing features of the present invention will become clearly apparent upon a reading of the ensuing detailed description together with the included drawing wherein:

BRIEF DESCRIPTION OF THE DRAWING FIGURES

FIG. 4 is a diagrammatic view of a cardiac pacer utilizing a cell according to the present invention; and FIG. 5 is a side elevational view with parts removed illustrating a cell according to another embodiment of the present invention.

DETAILED DESCRIPTION OF THE ILLUSTRATED EMBODIMENTS

Figure 1:
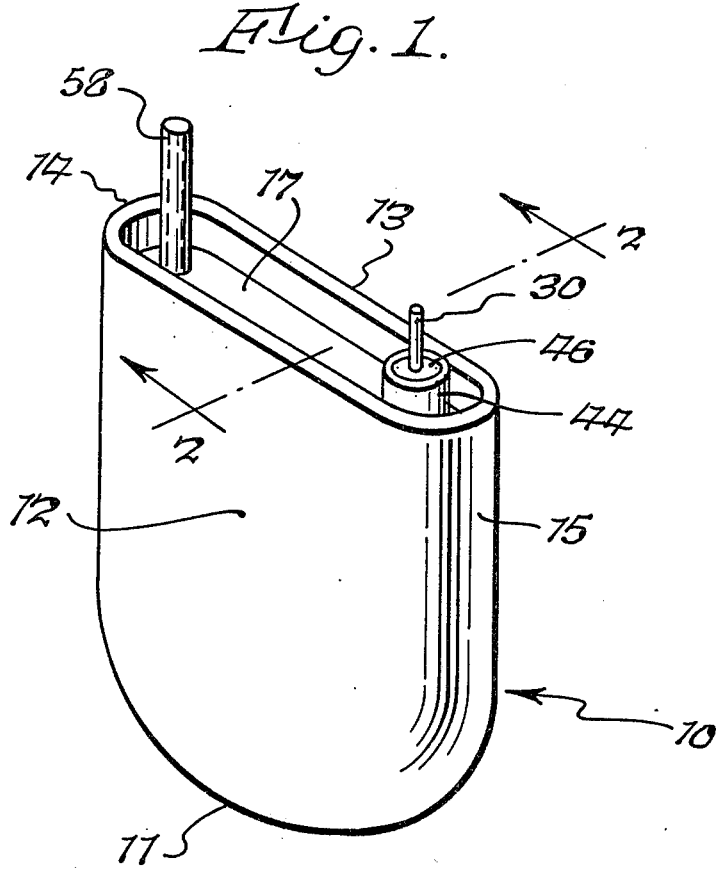
FIG. 1 is a perspective view of an alkali metal-halogen cell according to the present invention.

Referring now to FIG. 1, an alkali metal-halogen cell according to the present invention comprises a casing 10 of metal such as stainless steel which preferably is shaped or otherwise formed to be hollow and generally rectangular in shape of an integral construction including a curved bottom portion 11, spaced-apart planar side wall protions 12, 13 extending from the bottom portion, and spaced-apart curved end wall portions 14, 15 also extending from bottom portion 11 and joining corresponding ones of the side wall portions 12, 13. The bottom portion 11 is of compound curvature in that it is curved both in a direction between the side wall portions 12, 13 and also is curved in a direction between the end wall portions 14, 15. This latter curvature of bottom portion 11 is of the same degree as the curvature of the end wall portions 14, 15 thereby defining a continuous, curved surface around along the casing. The side wall portions 12, 13 are generally parallel. The casing has an opened top or end opposite the bottom portion 11 which is sealed closed by means of a lid 17 also of metal such as stainless steel.

Figure 2:
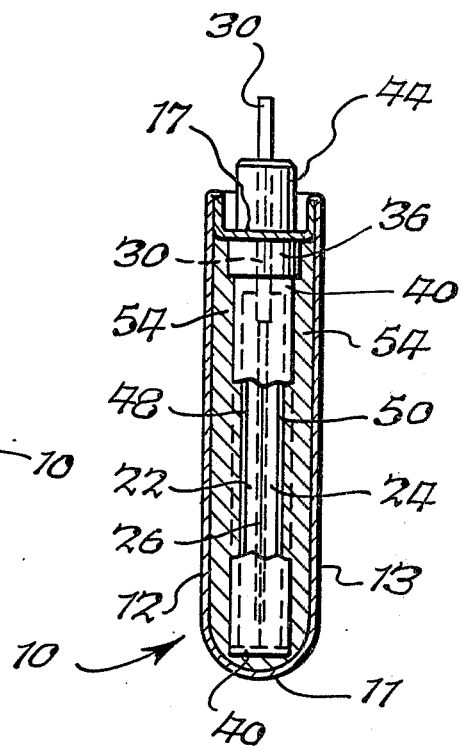
FIG. 2 is a sectional view taken about on line 2—2 in FIG. 1.
Figure 3:
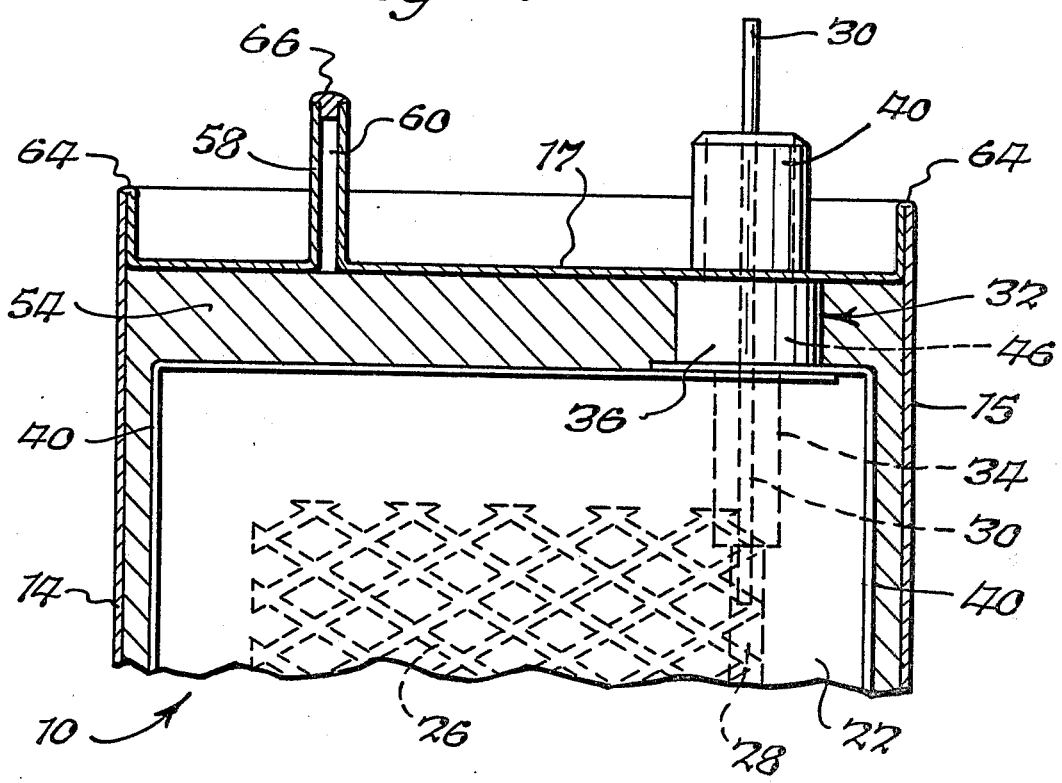
FIG. 3 is a fragmentary vertical sectional view with parts shown in elevation of the cell of FIG. 1.

Referring now to FIGS. 2 and 3, the cell of the present invention further includes anode means comprising a pair of alkali metal elements or plates 22, 24 having an anode current collector element 26 sandwiched or positioned therebetween. According to a preferred mode of the present invention, anode elements 22, 24 are of lithium. As shown in detail in FIG. 3, current collector 26 is a relatively thin, preferably a sheet of no. 12 mesh zirconium metal. A conductor strip 28 of nickel or suitable metal is spot welded to collector element 26 along one edge thereof, and an electrical conductor 30 which can be of nickel, or other suitable metal is welded at one end to the strip 28 and is of sufficient length allowing it to extend out from the casing for making external electrical connection thereto. Conductor 30 is sealed from the remainder of the cell by means including an insulator element generally designated 32 which surrounds lead 30 and has a first portion 34 which is sandwiched between the anode plates 22, 24 and a second or body portion 36 which is cylindrical and located between the anode plates and lid 17 when the cell is completed. The insulator 32 is of a material which in addition to being a non-conductor of electricity also is non-reactive with halogens. One form of material found to perform satisfactorily is a fluoropolymer material commercially available under the name Halar, a trademark of the Allied Chemical Company. Of course, other materials having these characteristics can be used for the insulator 32.

The anode assembly comprising the alkali metal elements 22, 24 and current collector 26 is fitted within an anode holding means or frame in the form of a strap 40 which embraces the anode assembly in a manner exposing at least one metal surface. Strap 40 is of the aforementioned Halar material or any similar material which is non-reactive with halogens. In the present illustration, strap 40 surrounds the peripheral edges of the anode elements or plates 22, 24 in a snug, sealing relationship. The opposite ends of strap 40 are provided with apertures of a size sufficient to receive the insulator portion 34, and these ends are overlapped adjacent the insulator portion 34 as shown in FIG. 3. A ferrule 44 of metal such as stainless steel encloses a further portion of lead 30. Ferrule 44 is threaded at one end (not shown) and is connected into insulator portion 36, the inner surface of which also is threaded. Ferrule 44 is of generally hollow cylindrical shape, and the region between ferrule 44 and conductor 30 is filled by a glass seal 46 formed therein to provide a metal-glass hermetical seal.

One illustrative method of forming the anode assembly is as follows. First there is provided a subassembly including lead 30 within the combination of insulator 32 and ferrule 44. Strap 40 then is assembled into place with the ends overlapped to align the openings therein which then are fitted onto insulator portion 34. The overlapping ends joined to insulator portion 34 can be sealed in place with a suitable cement which in non-reactive with halogens such as a cyanoacrylate cement commercially available under the name Permabond 101. Similarly, the junction between insulator portion 36 and the bottom portion of ferrule 44 can be cemented. Current collector 26, conducting strip 28 and the end of lead 30 are spot welded together whereupon lithium plates 22, 24 are positioned within strap 40 on opposite sides of the collector element 26 and insulator portion 34. The subassembly then is placed within a suitable fixture or support and is pressed together with a suitable force, for example about 3,000 lbs. The current collector 26, strip 28, insulator portion 34 and the portion of lead 30 contained therein are sealed within the lithium elements 22, 24. The material of strap 40 is pressure bondable to lithium with the result that the peripheral juncture at the edges of the lithium elements 22, 24 is enclosed or sealed by the strap 40. If desired, the junction between the inner surface of strap 40 and the periphery of lithium elements 22, 24 can be sealed further by the aforementioned cement. The completed anode assembly thus has two exposed surfaces which are oppositely directed or disposed.

When the anode assembly is completed, the exposed surfaces of the alkali metal elements 22 and 24 are provided with coatings 48 and 50, respectively, of an organic electron donor component material, and the nature of the coatings 48, 50 and their role in the cell of the present invention will be described in further detail presently. The completed anode assembly is positioned in casing 10 as shown in FIGS. 2 and 3, with the anode operative surfaces spaced from the inner surface of casing 10.

The cell of the present invention further comprises a cathode including a region of cathode material 54 within casing 10 and operatively contacting the exposed surfaces of the lithium elements 22, 24 and operatively contacting the inner surface of casing 10. Casing 10, being of electrically conducting material, serves as a cathode current collector. According to the present invention, the cathode material 54 comprises a mixture of at least two halogens wherein one of the halogens provides discharge of the cell at a first level of cell output voltage and the other halogen provides discharge of the cell at a second level of cell output voltage. In one aspect of the invention, the halogen which provides cell discharge at the higher level of cell output voltage is in the greater proportion by weight of the mixture. In another aspect thereof, the halogen which provides cell discharge at the lower level of cell output voltage is in the greater proportion by weight of the mixture. The mixed halogen cathode of the cell of the present invention will be described in detail presently.

The cell of the present invention further comprises an element 58 on the casing and having a passage 60 therethrough which at one end thereof is in communication with the interior of casing 10 and which at the other end is externally exposed. In particular, element 58 is in the form of a metal tube fixed to lid member 17. Tube 58 preferably is a separate element which is fitted at one end into an aperture provided through lid 17 and welded thereto. Alternatively, the lid 17 and tube 58 could be formed integrally from a single piece of metal. Lid member 17 is fitted into place in the open end of the casing and is welded at 64 around the peripheral edge thereof to the corresponding edge of the casing. In making the cell of the present invention, when cathode material is in liquid form, such as bromine, it is introduced through passage 60 in the filling element 58 to the interior of the casing and into operative relationship with the lithium anode. Then passage 60 is closed by suitable means, for example an element 66 which can be a plug of material which is non-reactive with halogens and which is sealed in place by suitable non-reactive cement. Also, sealing passage 60 can of course be accomplished by pinching or clamping the outer end of tube 58 and sealing it further by welding. The metal tube 58 preferably of nickel also serves as an electrical terminal inasmuch as the casing 10 serves as a cathode current collector.

The alkali metal-halogen cell according to the present invention operates in the following manner. As soon as the halogen-containing cathode material 54 operatively contacts an alkali metal anode element, a solid alkali metal-halogen electrolyte begins to form at the interface. In the cell illustrated in FIGS. 1-3, this occurs at the outer or oppositely disposed surfaces of the two anode elements 22 and 24. An electrical potential difference will exist between the anode lead 30 and the cathode terminal 58 because casing 10 is of electrically conductive material and operatively contacts the halogen-containing cathode material to serve as a cathode current collector. When anode elements 22, 24 are of lithium, the mechanism by which the foregoing is accomplished is believed to include migration of lithium ions through the electrolyte whereby lithium is the ionic species in the cell.

The cathode material 54 comprises a mixture of at least two halogens, and in one aspect of the present invention the halogen which provides cell discharge at the higher level of cell output voltage is in the greater proportion by weight of the mixture. For example, the mixture could comprise 95 percent bromine by weight and 5 percent iodine by weight. The cell 10 would have an open circuit voltage of about 3.4 volts for about 95 percent of cell life due to the more active halogen, i.e. bromine. The cell open circuit voltage then would drop to about 2.8 volts for the remaining 5 percent of cell lift after bromine depletion.

The two steps of pronounced plateaus in the output voltagetime characteristic provided by the mixed halogen cathode in the cell of the present invention is particularly advantageous when the cell is employed in an implanted cardiac pacer. The second plateau can give an early warning of impending pacer battery exhaustion. Since anticipated life of lithium-iodine and lithium bromine batteries for implanted cardiac pacers is about 120 months, the cathode of the foregoing example would provide one year of warning. Another advantage is that the second discharge step or plateau can soften the impact on the pacer system of the first discharge.

An illustrative method of making the cell when cathode material 54 comprises bromine and iodine according to the foregoing example is as follows. The anode assembly is positioned in the casing 10, and solid iodine preferably in pellet form also is placed in the casing. This is a relatively small amount of iodine, constituting about 5% by weight of the resulting cathode mixture according to the foregoing example. Lid 17 then is welded in place, and liquid bromine is introduced through element 58 to the interior of the casing 10, in operative contact with the iodine and the lithium anode. The amount of bromine is predetermined to constitute about 95% by weight of the resulting cathode mixture. Then element 58 is sealed closed at the outer end in a suitable manner. A cell wherein the cathode comprises a mixture of chlorine and iodine wherein chlorine is in the larger proportion by weight can be made according to the foregoing method by introducing liquid chlorine instead of bromine through element 58 into casing 10. A cell wherein the cathode comprises a mixture of chlorine and bromine wherein chlorine is in the larger proportion by weight can be made substantially according to the foregoing method wherein lid 17 is welded in place with no cathode component in casing 10, then the relatively small amount of liquid bromine is introduced to the casing through element 58 which then is temporarily closed, and the relatively large amount of liquid chlorine is introduced through the reopened element 58 which thereafter is permanently closed.

FIG. 4 is a diagrammatic view of a cardiac pacer 70 utilizing a cell according to the present invention. Pacer 70 includes a casing 72 of suitable material, preferably stainless steel, and a voltage source in the form of battery 74 including at least one cell similar to the cell of FIGS. 1-3 is located within casing 72. Battery 74 includes a lithium anode and a cathode comprising a mixture of two halogens, the halogen providing cell discharge at the higher level of cell output voltage being in the greater proportion by weight of the mixture. Battery 74 includes cathode and anode electrical terminals or leads 76 and 78, respectively, which are connected electrically to a pacer circuit means generally designated 80 including pulse forming means and related circuitry. The output terminals of circuit means 80 are connected by leads 82 and 84 to electrodes 86 and 88, at least one of which is adapted to be operatively connected to the heart of a patient. In particular, electrode 86 would be placed surgically in contact with the ventricle of the patient's heart and electrode 88, which can function as an indifferent or reference electrode, could be subcutaneously implanted at another part of the patient's body. Alternatively, electrode 88 also can be placed in contact with the patient's heart. The leads 82, 84 are enveloped by a moisture-proof and human body reaction-free material such as silicone rubber or suitable plastic.

In operation, the output voltage from battery 74 causes circuit 80 to generate output pulses of controlled pulse width or duration and frequency which pulses are conducted by leads 82 and 84 to electrodes 86 and 88, respectively, for stimulating the heart in a known manner. The circuit means 80 is of the type found in demand pacers, although other types can be employed. One pulse generator which can be used is disclosed in U.S. Pat. No. 3,508,167 although other circuits can be employed as well.

Battery 74 has a two step output voltage-time characteristic provided by the halogen mixture in the cathode. Battery 74 could have an open circuit voltage of about 3.4 volts for about 95 percent of battery life due to the more active halogen, i.e. bromine, whereupon the battery voltage would drop to about 2.8 volts for the remaining 5 percent of cell life after bromine depletion, as in the example described in detail in connection with FIGS. 1-3. One advantage of the two step output voltage characteristic is that the second plateau can give an early warning of pacer battery exhaustion. Another advantage is that the second discharge step or plateau can soften the impact on the pacer system of the first discharge.

According to another aspect of the present invention the halogen which provides cell discharge at the higher output voltage level is in the lesser proportion by weight of the resulting mixture. FIG. 5 illustrates such a cell wherein components identical to those of the cell of FIGS. 1-3 are identified by similar reference numerals provided with a prime superscript. Thus a casing 10', preferably of electrically conducting material such as stainless steel, contains an alkali metal anode, for example a pair of lithium plates, the one plate 22' being shown in FIG. 5. The anode is surrounded by the strap 40' at the peripheral edges thereof, and the anode electrical conductor 30' extends therefrom out through the casing and is enclosed and insulated by the insulator element 32' and ferrule 44'. The exposed or operative surfaces of the lithium plates are coated with an organic electron donor material as previously described. A solid pellet 92 of organic electron donor material containing about 5% to 10% by weight of the more active halogen, for example bromine, is placed in the casing in operative relationship with the anode. Preferably two such pellets or wafers are included in a cell, one adjacent each exposed face of the anode. Another solid pellet 94 of the other halogen, for example iodine, containing about 10% by weight of the more active halogen, i.e. bromine, also is placed in the casing adjacent the pellet 92. Preferably two such pellets or wafers are included in a cell, one adjacent each of the other pellets. Pellets 92, 94 each containing small amounts of bromine are prepared by a pressure forming operation wherein the pressure is 300-400 p.s.i. Then a quantity of the more active halogen, i.e. bromine, is introduced to the interior of casing 10'. In the present instance, lid 17' is sealed to the casing and liquid bromine is introduced through filling element 58' which then is sealed closed. The amount of bromine introduced is such that bromine is in the lesser proportion by weight of the cathode mixture.

The bromine immediately complexes into the organic electron donor of the pellet 92 thereby providing a cell having an output voltage of 3.45 volts. The complexed bromine also provides a conduction/diffusion path to utilize iodine in the cell reaction. In particular, injecting a relatively small amount or even just a trace of bromine makes the iodine plus organic electron donor material, i.e. poly-two-vinyl pyridine, fluid and conductive to permit iodine/poly-two-vinyl pyridine complexing to be initiated. In other words the complex of iodine and poly-two-vinyl pyridine is formed in situ in the casing 10. The bromine initiates the complexing reaction, and after the system is conductive and semifluid, the iodine reactions, i.e. formation of complex and formation of electrolyte, proceed normally even though the initial bromine is gone. Thus solid iodine and solid poly-two-vinyl pyridine are utilized in a cell construction in a manner such that the two are complexed in situ. For this in situ complexing, the pellets 92, 94 need not contain bromine. In addition, the discharge plateau provided by the more active halogen, i.e. the bromine, is very small, possibly about 1% of the total and this permits a nondestructive test for self-discharge in stored batteries. In particular, any significant self-discharge would use up the trace of bromine first, resulting in an easily detected drop in cell voltage. A cell of the type described can be made using chlorine instead of bromine.

In the cell according to the present invention, it is important that the halogen-containing cathode material is not allowed to come in contact directly with any portion of the electrical conducting means connected to the elements of the anode, in particular anode current collector 26 and leads 28, 30 shown in FIGS. 1-3. Otherwise, this will cause an electronic conduction between the cathode material and the anode current collector 26 or leads 28, 30 creating an electrical short circuit condition in the cell. In particular, any migration of the halogen-containing cathode material directly to anode current collector 26 or directly to leads 28, 30 instead of first reacting with an element of the anode, i.e. one of the lithium elements, will result in a condition of electronic conduction thereby creating a short circuit in the cell. On the other hand, when the halogen-containing cathode material contacts only the lithium or other alkali metal portion of the anode this gives rise first to a condition of ionic conduction and results in proper cell operation.

In the cell of the present invention, all parts of the anode current collector 26 and leads 28, 30 are sealed from the cathode material and from the metal casing. Anode current collector 26 and its connection through strip 28 to lead 30 are sealed within the sandwiched or pressure bonded assembly of lithium plates 22, 24. This seal is enhanced by the strap 40 which is of Halar or similar materials which is non-reactive with halogens such as iodine and bromine.

The foregoing arrangement together with the provision of insulator 32 and ferrule 44 with glass seal 46 provides an anode structure which is completely sealed with the exception of the oppositely-directed operative lithium surface portions of the anode which are available to the cathode material. All parts of anode current collector 26 and leads 28, 30 are shielded from the cathode material and from the cell casing. Furthermore, the sealed anode assembly can be completed before the entire cell is assembled for efficiency in manufacturing. The foregoing advantages are provided in a cell which is relatively simple in construction.

The material of coatings 48 and 50 on lithium elements 22 and 24, respectively, is an organic electron donor material of the group of organic compounds known as charge transfer complex donors. The material of the coatings can be the organic electron donor material introduced into the cell casing prior to introducing the halogen which then reacts to form the charge transfer complex of the cathode material 54, but other materials can be employed. A preferred material for the coatings is polyvinyl pyridine and it is applied to the exposed surfaces of lithium elements 22 and 24 in the following manner. A solution of poly-2-vinyl pyridine polymer in anhydrous benzene or other suitable solvent is prepared. The poly-2-vinyl pyridine is readily commercially available. The solution is prepared with 2-vinyl pyridine present in the range from about 10% to about 20% by weight with a strength of about 14% by weight of 2-vinyl-pyridine being preferred. While 2-vinyl pyridine, 4-vinyl pyridine and 3-ethyl 2-vinyl pyridine can be used, 2-vinyl pyridine is preferred because of its more fluid characteristics in solution. When the solution is prepared at a strength below about 10% the resulting coating can be undesirably too thin and when the solution is prepared at a strength greater than about 20% the material becomes difficult to apply. The solution is applied to the exposed surface of each lithium plate in a suitable manner, for example simply by application with a brush. The presence of the anhydrous benzene serves to exclude moisture thereby preventing any adverse reaction with the lithium plate. The coated anode then is exposed to a desiccant in a manner sufficient to remove the benzene from the coating. In particular the coated anode is placed in a chamber with barium oxide solid material for a time sufficient to remove the benzene, which can be in the neighborhood of 24 hours. The foregoing procedure can be repeated to provide multiple coatings or layer, for example three, on each lithium plate.

It is therefore apparent that the present invention accomplishes its intended objects. While several embodiments of the present invention have been described in detail, this is for the purpose of illustration, not limitation.

I claim:

1. A cardiac pacer comprising:
   (a) pulse forming means having an input and an output;
   (b) a pair of electrodes connected to the output of said pulse forming means, at least one of which is adapted to be operatively coupled to a patient's heart; and
   (c) a voltage source connected to the input of said pulse forming means and comprising a battery having an alkali metal anode, a solid alkali metal-halogen electrolyte and a cathode comprising a mixture of two halogens, one of said halogens providing a discharge of said battery at a first level of battery output voltage and the other of said halogens providing discharge of said battery at a second level of battery output voltage.

2. A cardiac pacer according to claim 1, wherein said halogens are in different proportions by weight in said mixture.

3. A cardiac pacer according to claim 1, wherein the one of said halogens which provides battery discharge at the higher level of battery output voltage is in the greater proportion by weight of said mixture.

4. A cardiac pacer according to claim 1, wherein said battery anode is of lithium.

5. A cardiac pacer according to claim 1, wherein said battery anode is of lithium and said battery cathode comprises a mixture of bromine and iodine.

6. A cardiac pacer according to claim 5, wherein bromine comprises about 95 percent by weight of said mixture and iodine comprises about 5 percent by weight of said mixture.

* * * * *

UNITED STATES PATENT AND TRADEMARK OFFICE
CERTIFICATE OF CORRECTION

PATENT NO. : 4,135,519
DATED : January 23, 1979
INVENTOR(S) : Wilson Greatbatch

It is certified that error appears in the above-identified patent and that said Letters Patent are hereby corrected as shown below:

Claim 1(c), lines 5 and 6, "providing a discharge"

should be --providing discharge--.

Signed and Sealed this

Fifth Day of June 1979

[SEAL]

Attest:

RUTH C. MASON
Attesting Officer

DONALD W. BANNER
Commissioner of Patents and Trademarks